(12) United States Patent
Yu

(10) Patent No.: US 12,364,853 B2
(45) Date of Patent: Jul. 22, 2025

(54) BLOOD PUMP

(71) Applicant: SHENZHEN CORE MEDICAL TECHNOLOGY CO., LTD., Guangdong (CN)

(72) Inventor: Shunzhou Yu, Guangdong (CN)

(73) Assignee: SHENZHEN CORE MEDICAL TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 17/781,914

(22) PCT Filed: Nov. 17, 2021

(86) PCT No.: PCT/CN2021/131267
§ 371 (c)(1),
(2) Date: Jun. 2, 2022

(87) PCT Pub. No.: WO2022/134956
PCT Pub. Date: Jun. 30, 2022

(65) Prior Publication Data
US 2023/0310834 A1 Oct. 5, 2023

(30) Foreign Application Priority Data
Dec. 22, 2020 (CN) .......................... 202011525102.7

(51) Int. Cl.
*A61M 60/00* (2021.01)
*A61M 60/403* (2021.01)
(Continued)

(52) U.S. Cl.
CPC ........ *A61M 60/403* (2021.01); *A61M 60/804* (2021.01); *A61M 60/818* (2021.01); *A61M 60/216* (2021.01)

(58) Field of Classification Search
None
See application file for complete search history.

(56) References Cited

U.S. PATENT DOCUMENTS 7,011,620 B1 * 3/2006 Siess ..................... A61M 60/13
600/16
2006/0071576 A1 4/2006 Cho
(Continued)

FOREIGN PATENT DOCUMENTS

CN 101873870 A 10/2010
CN 108883216 A 11/2018
(Continued)

OTHER PUBLICATIONS

European Search Report for European Application No. EP 21899279.0, Completed by the European Patent Office, Dated Oct. 31, 2024, 10 pages.

(Continued)

*Primary Examiner* — Sana Sahand
(74) *Attorney, Agent, or Firm* — Brooks Kushman P.C.

(57) ABSTRACT

The present application discloses a blood pump, the blood pump includes a cannula having a blood flow inlet and a blood flow outlet; an impeller is arranged in the cannula; a drive unit includes a casing connected to the cannula, and a rotor and a stator arranged in the casing, the rotor includes a rotating shaft and a magnet provided on the rotating shaft, the stator includes posts arranged around the axis of the rotating shaft and a coil winding around the peripheries of the posts, the coil winding can generate rotating magnetic field interacts with the magnet to rotate the rotating shaft, and the magnet and the posts are arranged at intervals along the extending direction of the rotating shaft.

17 Claims, 15 Drawing Sheets

(51) Int. Cl.
*A61M 60/804* (2021.01)
*A61M 60/818* (2021.01)
*A61M 60/216* (2021.01)

(56) References Cited

U.S. PATENT DOCUMENTS

| | | | | |
|---|---|---|---|---|
| 2009/0118567 | A1* | 5/2009 | Siess | F04D 13/06 600/16 |
| 2011/0238172 | A1 | 9/2011 | Akdis | |
| 2016/0303299 | A1* | 10/2016 | Muller | A61M 60/174 |
| 2019/0060539 | A1* | 2/2019 | Siess | A61M 60/13 |
| 2019/0298902 | A1* | 10/2019 | Siess | A61M 60/221 |
| 2020/0076271 | A1* | 3/2020 | Sconzert | A61M 60/818 |
| 2021/0001027 | A1* | 1/2021 | Kirchhoff | A61M 60/174 |

FOREIGN PATENT DOCUMENTS

| | | |
|---|---|---|
| CN | 109414533 A | 3/2019 |
| CN | 111770765 A | 10/2020 |
| CN | 111971080 A | 11/2020 |
| CN | 112472999 A | 3/2021 |
| CN | 215025224 U | 12/2021 |
| CN | 215084231 U | 12/2021 |
| JP | 2000511455 A | 9/2000 |
| JP | 2007507257 A | 3/2007 |
| JP | 2008245503 A | 10/2008 |
| JP | 2013536021 A | 9/2013 |
| JP | 2015508678 A | 3/2015 |
| JP | 2019022428 A | 2/2019 |
| JP | 2019129637 A | 8/2019 |
| JP | 2020534085 A | 11/2020 |
| WO | 2006068042 A1 | 6/2006 |
| WO | 2019180221 A1 | 9/2019 |
| WO | 2020187797 A1 | 9/2020 |

OTHER PUBLICATIONS

National Intellectual Property Administration, PRC, Office Action for Chinese Patent Application No. 202011525102.7 dated Oct. 10, 2024. 6 pages.

* cited by examiner

BLOOD PUMP

CROSS REFERENCE TO RELATED APPLICATION

The present application is a National phase of international patent application No. PCT/CN2021/131267 with an international filling date of Nov. 27, 2021, and further claims priority of Chinese Invention Patent application, with application No. 202011525102.7, filed on Dec. 22, 2020, the contents of all of the aforementioned applications are incorporated herein by reference.

TECHNICAL FIELD

The present application relates to the technical field of medical devices, and more particularly to a blood pump.

BACKGROUND

The statements herein merely provide background information related to the present application and do not necessarily constitute prior art.

An intravascular blood pump, designed to be inserted percutaneously into a blood vessel of a patient, such as an artery or vein in the thigh or axilla, can be advanced into the heart of the patient to function as a left ventricular assist device or a right ventricular assist device. Therefore, the intravascular blood pump may also be referred to as the intracardiac blood pump.

The blood pump mainly includes an impeller and a motor that drives the impeller to rotate. When the motor drives the impeller to rotate, the impeller can rotate around its axis, and the blood is transported from the blood flow inlet of the blood pump to the blood flow outlet. When the motor works, a rotating magnetic field is generated, and the impeller is provided with magnet that interacts with the rotating magnetic field, so that the impeller rotates around its axis. However, the magnet on the impeller will increase the weight of the impeller and reduce the pumping efficiency of the impeller; in addition, the size and shape design of the impeller will be limited by the magnet on it, which increases the processing difficulty of the impeller.

Technical Problem

One of objects of embodiments of the present application is to provide a blood pump, which can at least solve the technical problem that pumping efficiency of the impeller is lower, and processing difficulty of the blood pump is high.

SUMMARY

An embodiment of the present application provides a blood pump, which includes:
- a cannula, provided with a blood flow inlet and a blood flow outlet;
- an impeller, disposed in the cannula;
- a drive unit, capable of driving the impeller to rotate and including: a casing, connected to the cannula; a rotor, comprising a rotating shaft and a magnet, wherein the rotating shaft is partially accommodated in the casing, and partially extends to an outside of the casing and is connected with the impeller; the magnet is accommodate in the casing and arranged on the rotating shaft; and a stator, comprising a plurality of posts arranged around an axis of the rotating shaft, and a coil winding around peripheries of the posts, wherein the coil winding capable of generating a rotating magnetic field that interacts with the magnet to rotate the rotating shaft, and the magnet and the posts are arranged at intervals along an extending direction of the rotating shaft.

Beneficial Effects

The blood pump provided by the embodiments of the present application has at least the following beneficial effects:

Compared with arranging the magnet directly on the impeller, the present application arranges the magnet on the rotating shaft, so that the axial distance between the magnet and the stator is not disturbed by other components, especially the influence of the axial distance between the impeller and the thickness of the casing, such that a small axial distance between the magnet and the stator is easy to be obtained. When the axial distance between the magnet and the posts of the stator decreases, the magnetic density between the magnet and the posts will increase, and the output power and torque of the drive unit will accordingly increase, therefore, in the present application, the magnet and the posts are arranged on the rotating shaft long an axial direction at intervals, so that there is a greater magnetic density between the two and the output power of the drive unit is increased. Moreover, since the magnet is arranged on the rotating shaft, the size and shape design of the impeller of the present application are not affected by the magnet, the design of the impeller is more flexible, and the processing difficulty of the impeller is reduced.

BRIEF DESCRIPTION OF THE DRAWINGS

In order to illustrate the technical solutions in the embodiments of the present application more clearly, the following briefly introduces the accompanying drawings that are used in the description of the embodiments or exemplary technologies. Obviously, the drawings in the following description are only for the present application. In some embodiments, for those skilled in the art, other drawings can also be obtained according to these drawings without any creative effort.

DETAILED DESCRIPTION

Figure 1:
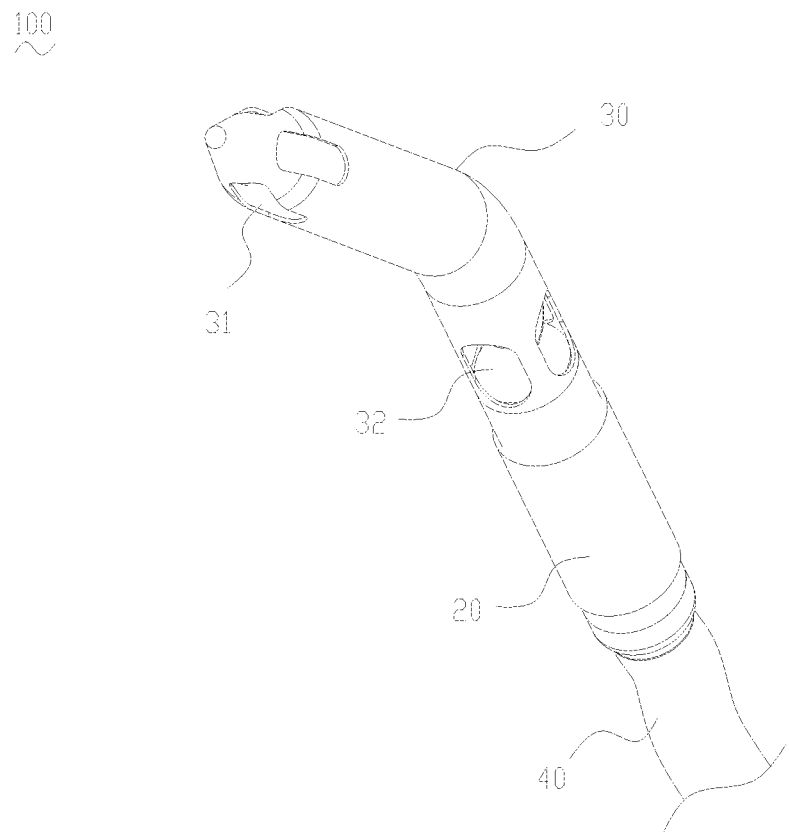
FIG. 1 is a perspective view of a blood pump provided in a first embodiment of the present application.

In order to make the purpose, technical solutions and advantages of the present application more clearly understood, the present application will be described in further detail below with reference to the accompanying drawings and embodiments. It should be understood that the specific embodiments described herein are only used to explain the present application, but not to limit the present application.

It should be noted that when a component is referred to as being "fixed to" or "disposed on" another component, it can be directly on the other component or indirectly on the other component. When an element is referred to as being "connected to" another element, it can be directly or indirectly connected to the other element. The orientation or positional relationship indicated by the terms "upper", "lower", "left", "right", etc. is based on the orientation or positional relationship shown in the drawings, and is only for the convenience of description, rather than indicating or implying the referred device or the elements must have a specific orientation, be constructed and operated in a specific orientation, and therefore should not be construed as a limitation on the present application, and those skilled in the art can understand the specific meanings of the above terms according to specific situations. The terms "first" and "second" are only used for the purpose of description, and should not be understood as indicating or implying relative importance or implying indicating the number of technical features. "a plurality of" means two or more, unless expressly specifically limited otherwise.

In order to illustrate the technical solutions provided in the present application, the following detailed description is given in conjunction with the specific drawings and embodiments. In the field of interventional medicine, the end of the device close to the operator is usually defined as the proximal end, and the end farther from the operator is defined as the distal end.

Figure 2:
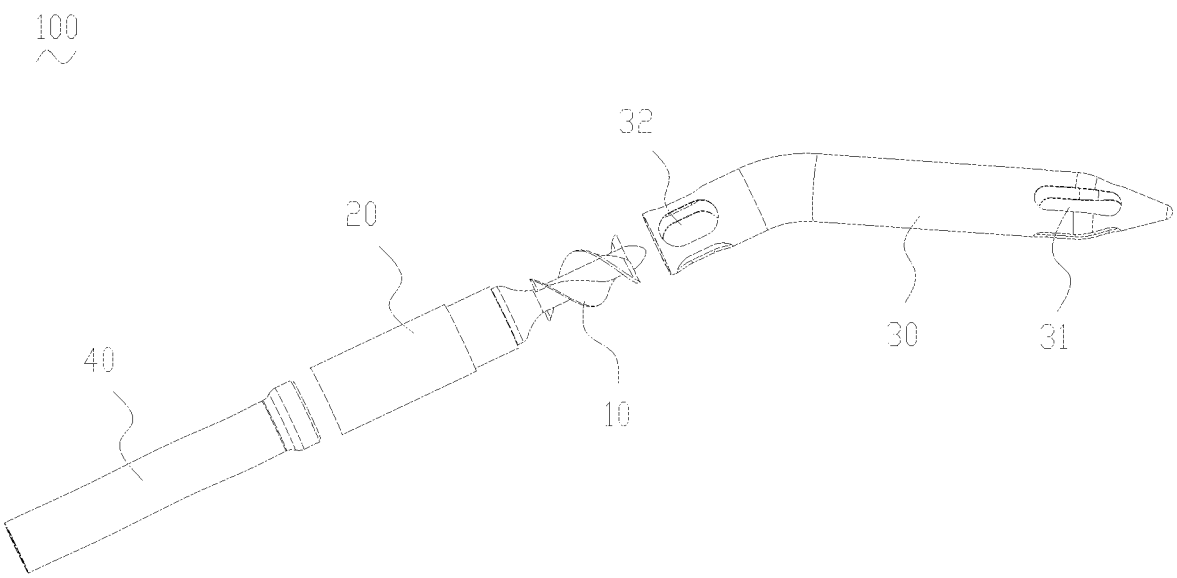
FIG. 2 is an exploded view of the blood pump shown in FIG. 1.

Referring to FIGS. 1 and 2, a first embodiment of the present application provides a blood pump 100, which includes an impeller 10, a drive unit 20, a cannula 30 and a catheter 40. The impeller 10 is rotatably arranged in a cannula 30, the drive unit 20 can drive the impeller 10 to rotate, the proximal end of the cannula 30 is connected to the distal end of the drive unit 20, and the distal end of the catheter 40 is connected to the proximal end of the drive unit 20. The catheter 40 is configured for accommodating supply pipelines, such as cleaning pipelines, and wires electrically connected to the drive unit 20. The cannula 30 is provided with a blood flow inlet 31 and a blood flow outlet 32. When the impeller 10 works, blood enters the cannula 30 from the blood flow inlet 31 and is discharged from the blood flow outlet 32 along the blood flow channel in the cannula 30.

Figure 3:
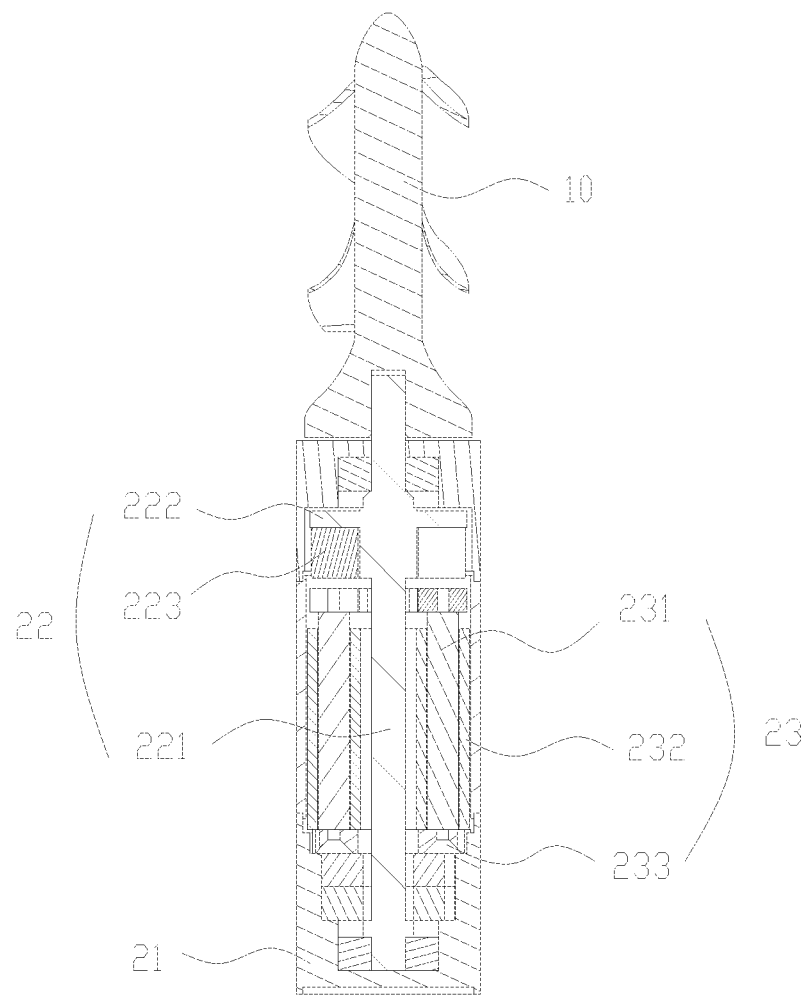
FIG. 3 is a sectional view of a connection between an impeller and a drive unit of the blood pump shown in FIG. 1.

Referring to FIG. 3, the drive unit 20 is located outside the cannula 30 and is fixedly connected with the proximal end of the cannula 30. The drive unit 20 includes a casing 21, and a rotor 22 and a stator 23 arranged in the casing 21. The casing 21 is connected to the cannula 30, and specifically, the distal end of the casing 21 is fixedly connected to the proximal end of the cannula 30. The rotor 22 is partially accommodated in the casing 21, and the rotor 22 can rotate relative to the casing 21. The rotor 22 includes a rotating shaft 221 and a magnet 223 mounted on the rotating shaft 221. The rotating shaft 221 is partially accommodated in the casing 21, and partially extends to the outside of the casing 21 and is fixedly connected to the impeller 10. The magnet 223 is accommodated in the casing 21, and the magnet 223 is disposed on the rotating shaft 221. The stator 23 includes a plurality of posts 231 arranged around the axis of the rotating shaft 221, and coil windings 232 surrounding the peripheries of the posts 231. The coil windings 232 can generate a rotating magnetic field interacting with the magnet 223 to rotate the rotating shaft 221. The magnet 223 and the posts 231 are arranged at intervals along the extending direction of the rotating shaft 221.

In some embodiments, the axial distance between the magnet 223 and the posts 231 is ranged from 0.1 mm to 2 mm, so that there is a greater magnetic density between the magnet 223 and the posts 231, thereby increasing the output power of the drive unit 20. For example, it is 0.1 mm-0.5 mm. In the present application, the extending direction (ie, the extending direction of the axis of the rotation shaft) parallel to the rotation shaft 221 is defined as the axial direction, and the direction perpendicular to the axial direction is defined as the radial direction.

It should be noted that, when the end surface of each magnet 223 or each post 231 is a sloped surface or a non-flat surface, the "axial distance" between the magnet 223 and the posts 231 here refers to the axial distance between n the most proximal point of the magnet 223 and the most distal point of the post 231; alternatively, the axial distance between the most distal point of the magnet 223 and the most proximal point of the post 231.

Compared with the prior art in which the magnet is directly disposed on the impeller, the present application disposes the magnet 223 on the rotating shaft 221, so that the axial distance between the magnet 223 and the stator 23 is not disturbed by other components, especially the influence of the axial distance between the impeller 10 and the casing 21 of the drive unit 20 and the thickness of the casing 21, such that a smaller axial distance between the magnet 223 and the stator 23 can be obtained. When the axial distance between the magnet 223 and the posts 231 of the stator 23 decreases, the magnetic density between the magnet 223 and the posts 231 increases, and the output power of the drive unit 20 increases accordingly. Therefore, in the present application, the magnet 223 and the posts 231 are arranged on the rotating shaft 221 at an axial interval, and since the magnet 223 is arranged on the rotating shaft 221, the size and shape design of the impeller 10 of the present application are not affected by the magnet 223. The design of the impeller 10 is more flexible, and the processing difficulty of the impeller 10 is reduced.

In addition, in the present application, the magnet 223 and the posts 231 are arranged at intervals along the extending direction of the rotating shaft 221 (ie, along the axial direction), and the rotating shaft 221 is driven to rotate by the direct drive of the axial magnetic flux, which can reduce the radial size of the drive unit 20. That is, the present application can increase the output power and load torque of the drive unit 20 on the basis of reducing the overall radial size of the drive unit 20.

The structure of the drive unit 20 will be specifically described below.

Figure 4:
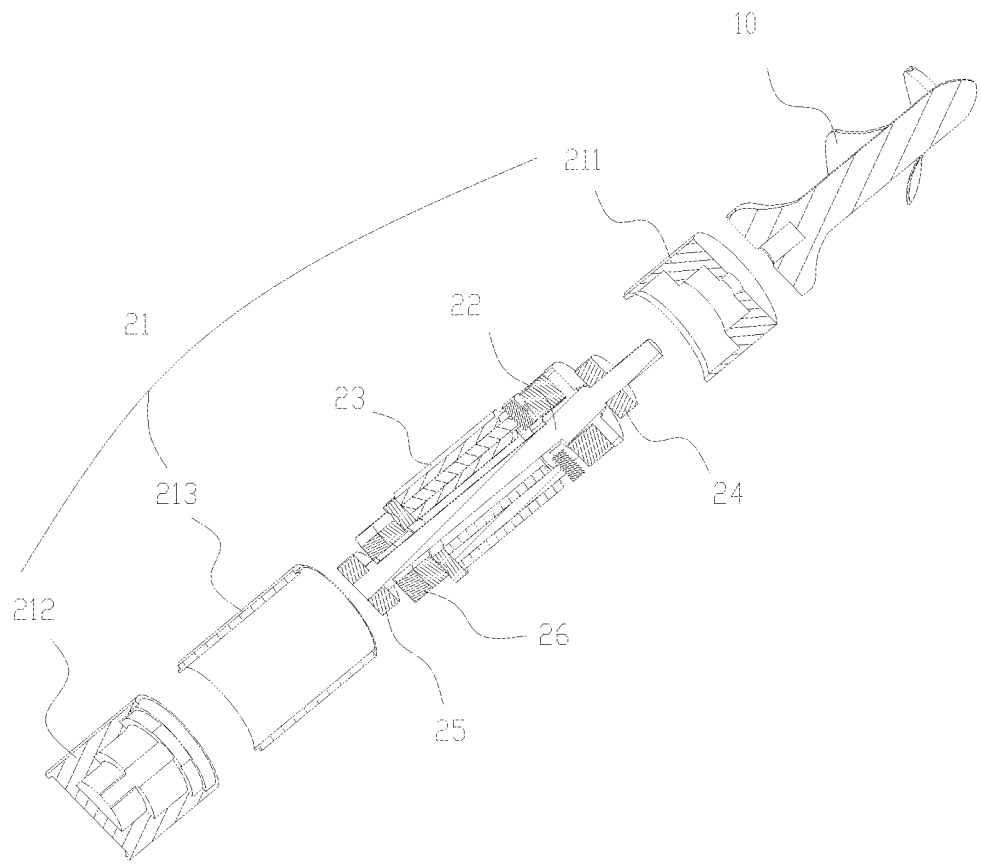
FIG. 4 is an exploded view of the impeller and the drive unit of the blood pump shown in FIG. 3.
Figure 5:
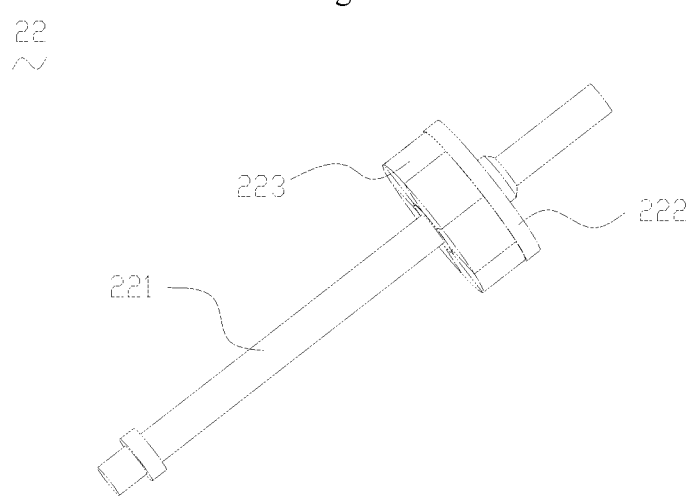
FIG. 5 is a schematic structural view of a rotor of the drive unit shown in FIG. 3.

Referring to FIG. 4, the drive unit 20 includes a casing 21, a rotor 22, a stator 23, a distal bearing 24, a proximal bearing 25 and a control member 26 respectively mounted in the casing 21. Referring to FIG. 5, the rotor 22 includes a rotating shaft 221, a flywheel 222 and a magnet 223. The distal end of the rotating shaft 221 extends out of the casing 21 and is fixedly connected with the impeller 10. The flywheel 222 is fixed on the rotating shaft 221. The magnet 223 is fixed on the flywheel 222, and the rotating magnetic field generated by the stator 23 capable of interacting with the magnet 223, so that the magnet 223 and the flywheel 222 fixedly connected with the magnet 223 rotate together, thereby driving the rotating shaft 221 and the impeller 10 to rotate.

In some embodiments, the magnet 223 includes a plurality of magnetic units surrounding the rotating shaft 221, and two adjacent magnetic units are arranged at intervals. If the gap between the two adjacent magnetic units is too small, the innermost magnetic field extending in the adjacent two magnetic units cannot interact with the rotating magnetic field generated by the stator 23, affecting the rotation speed of the rotating shaft 221. Therefore, by arranging two adjacent magnetic units at intervals, and adjusting the size of the gap between the two adjacent magnetic units according to the size of the axial distance between the magnet 223 and the stator 23. In the embodiment, the magnet 223 is composed of six magnetic units, and the six magnetic units are arranged at intervals around the axis of the rotating shaft 221. Each magnetic unit is a fan-shaped magnet, so that the magnet 223 has a substantially annular structure. It can be understood that, in other embodiments, the magnet 223 may also be composed of more or less magnetic units, such as two, four, eight, or ten.

Figure 6:
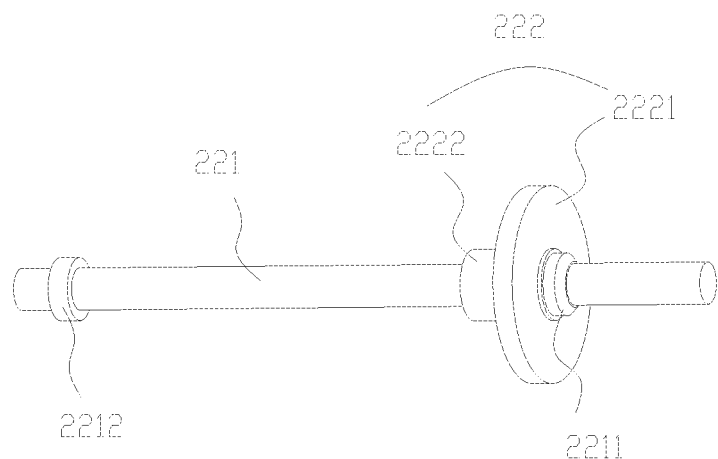
FIG. 6 is a schematic structural view of a rotating shaft and a flywheel of the rotor shown in FIG. 5.

Referring to FIG. 6, the flywheel 222 includes a body portion 2221 and a mounting boss 2222. The body portion 2221 has a substantially disc-shaped structure, such as a disc structure. The mounting boss 2222 is fixedly connected to the body portion 2221, the mounting boss 2222 is located on the side of the body portion 2221 facing the stator 23, and the rotating shaft 221 is fixedly penetrated through the body portion 2221 and the mounting boss 2222. The magnet 223 is fixed on the body portion 2221 and disposed around the outer periphery of the mounting boss 2221.

Specifically, the mounting boss 2222 is located in the middle of the body portion 2221. One end of the mounting boss 2222 is fixedly connected with the body portion 2221, and the other end extends away from the body portion 2221 along the extending direction of the rotating shaft 221. The outer diameter of the mounting boss 2222 is larger than the outer diameter of the rotating shaft 221, but smaller than the outer diameter of the body portion 2221. By arranging the mounting boss 2221 on the body portion 2221, the magnet 223 can be easily assembled and positioned, so that the magnet 223 can be better fixed on the body portion 2221.

In the present application, the flywheel 222 is arranged on the rotating shaft 221, and the magnet 223 is fixed on the flywheel 222, and the rotating shaft 221 is driven to rotate by the flywheel 222, which can increase the connection strength between the magnet 223 and the rotating shaft 221, and improve the stability of the rotating shaft 221 when it rotates. In the embodiment, the flywheel 222 and the rotating shaft 221 are integrally formed. In other embodiments, the flywheel 222 may also be fixedly connected to the rotating shaft 221 by other means, such as bonding, welding, and the like.

It can be understood that the flywheel 222 in the embodiment is only used as an example and does not limit the present application. The flywheel 222 of the present application may also have other structures as long as the magnet 223 can be fixed on the rotating shaft 221. For example, in other embodiments, the flywheel 222 only includes the body portion 2221, and the magnet 223 is fixed on the side of the body portion 2221 facing the stator 23; alternatively, the flywheel 222 only includes the mounting boss 2222, and the magnet 223 is fixed on the mounting boss 2222; alternatively, the flywheel 222 is composed of a plurality of supporting rods arranged at intervals around the axis of the rotating shaft 221, one end of each supporting rod is fixed on the rotating shaft 221, and the other end extends away from a side of the rotating shaft 221 in the radial direction, the number of supporting rods is the same as the number of magnetic units, and one magnetic unit is fixed on the side of each supporting rod close to the stator 23. Alternatively, in other embodiments, the flywheel 222 may not be provided on the rotating shaft 221, and the magnet 223 may be directly fixed on the rotating shaft 221; alternatively, the rotating shaft 221 is provided with a fixing groove, and the magnet 223 is assembled in the fixing groove.

Figure 7:
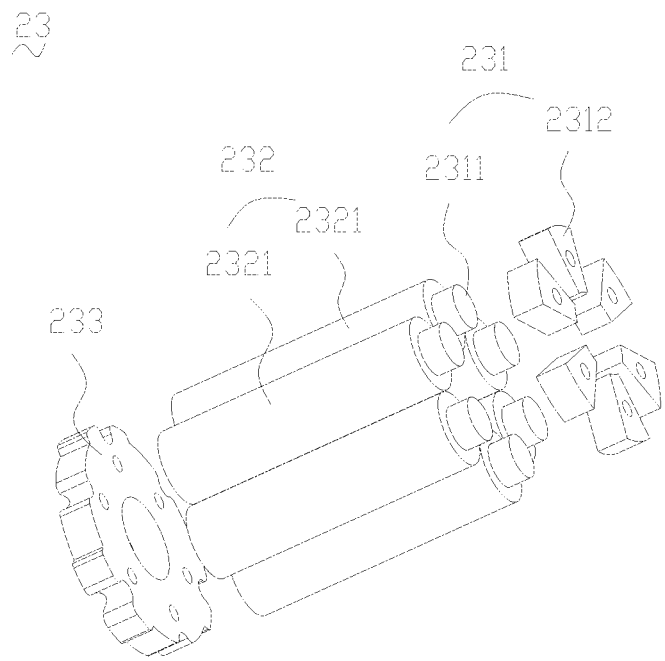
FIG. 7 is an exploded view of a stator of the drive unit shown in FIG. 3.

Referring to FIG. 7, the stator 23 includes a plurality of posts 231 arranged around the axis of the rotating shaft 221, coil windings 232 surrounding the peripheries of the posts 231, and a back plate 233. The center of the stator 23 has a channel penetrating in the axial direction, and the rotating shaft 221 is rotatably penetrated through the channel. A plurality of posts 231 are arranged around the axis of the rotating shaft 221 to form an annulus-like structure, and the rotating shaft 221 passes through the center of the annulus-like structure. Each post 231 serves as magnetic core, which is made of soft magnetic material, such as cobalt steel or the like.

Each post 231 includes a rod portion 2311, and a head portion 2312 fixed at one end of the rod portion 2311, and the head portion 2312 is magnetically coupled with the magnet 223. The coil winding 232 includes a plurality of coils 2321, the number of the coils 2321 is the same as the number of the posts 231, and a corresponding coil 2321 is surrounded on the outer circumference of each rod 2311. The coil winding 232 is sequentially controlled by a control unit (not shown) to create a rotating magnetic field for driving the magnet 223. The back plate 233 is connected with the end of the rod portion 2311 away from the head portion 2312 to close the magnetic flux circuit, increase the magnetic flux, improve the coupling ability, and help the blood pump to increase the output power of the drive unit 20 on the basis of reducing the overall radial size. The back plate 233 is also made of a soft magnetic material, such as cobalt steel, which is the same material as the posts 231.

Figure 8:
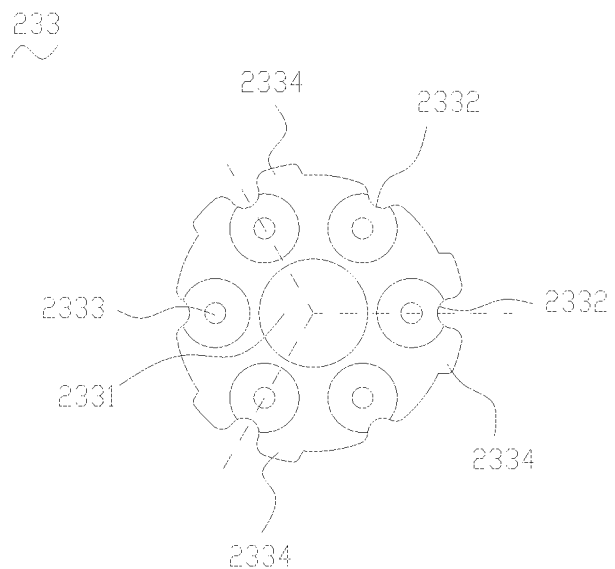
FIG. 8 is a schematic structural view of a back plate of the stator shown in FIG. 7.

Referring to FIG. 8, the back plate 233 is provided with a first mounting hole 2331, the first mounting hole 2331 is in clearance fit with the rotating shaft 221, and the rotating shaft 221 is rotatably penetrated through the first mounting hole 2331. The back plate 233 is also provided with a groove 2332 for the connection wires of the coil winding 232 to pass through. The back plate 233 is further provided with through holes 2333 penetrating in the axial direction. During assembly, glue can be poured between the back plate 233 and the rod portion 2311 through the through holes 2333, so that the rod portion 2311 and the back plate 233 are fixedly connected. In the embodiment shown in FIG. 8, the through holes 2333 are counterbored structures, the number of the through holes 2333 is the same as that of the rod portions 2311, and each of the through holes 2333 corresponds to the position of the rod portion 2311. It can be understood that, in other embodiments, the through holes 2333 can also be other hole structure forms, as long as it can penetrate the back plate 233; In this way, the rod portion 2311 is fixedly connected with the back plate 233.

Both the distal bearing 24 and the proximal bearing 25 are fixedly accommodated in the casing 21, the distal bearing 24 and the proximal bearing 25 are arranged along the axis of the rotating shaft 221, and the distal bearing 24 is closer to the impeller 10 than the proximal bearing 25, the rotating shaft 221 passes through the distal bearing 24 and is connected with the proximal bearing 25. The control member 26 is fixedly accommodated in the casing 21, and the control member 26 is electrically connected to the coil winding 232.

Figure 9:
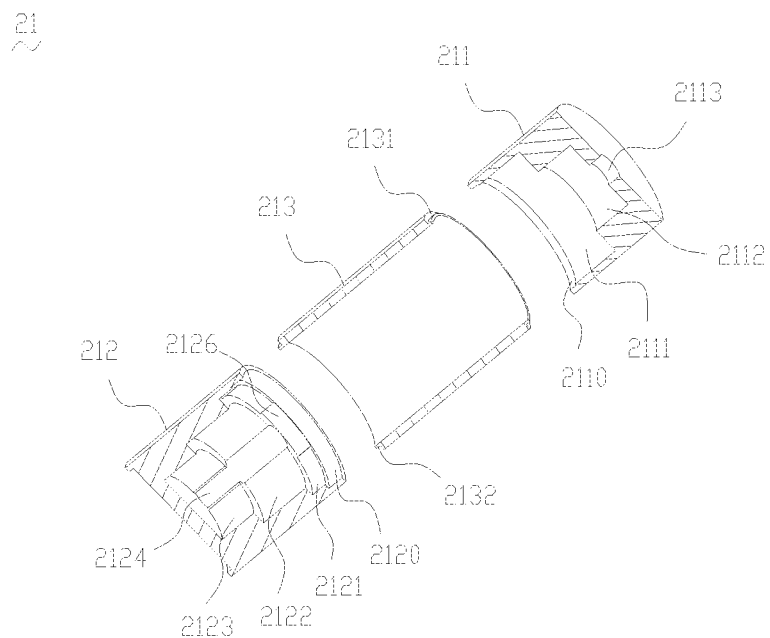
FIG. 9 is an exploded view of a casing of the drive unit shown in FIG. 3.

Referring to FIG. 9, specifically, the casing 21 includes a first casing 211, a second casing 212 and a third casing 213. The third casing 213 is sleeved outside the stator 23, the first casing 211 and the second casing 212 are respectively connected to both ends of the third casing 213, and the rotating shaft 221 passes through the first casing 211 and is connected to the impeller 10. Specifically, the first casing 211, the third casing 213 and the second casing 212 are arranged in sequence along the axis of the rotating shaft 221. The first casing 211 is close to the distal end of the rotor 22, and the second casing 212 is close to the proximal end of the rotor 22. The first casing 211 is generally a structure with one end open and the other end closed. The distal end of the rotating shaft 221 protrudes from the first casing 211 and is connected to the impeller 10. Along the direction from the proximal end to the distal end of the first casing 211, the first casing 211 is provided with a first connecting groove 2110, a first mounting groove 2111, a first limiting groove 2112 and a through hole 2113 that communicate with each other.

The first connecting groove 2110 is configured for connecting with the third casing 213. During assembly, the distal connection member 2131 of the third casing 213 is inserted into the first connecting groove 2110, so that the first casing 211 and the third casing 213 are fixedly connected. The first mounting groove 2111 is configured to accommodate the magnet 223 and the flywheel 222, and the magnet 223 and the flywheel 222 are rotatably accommodated in the first mounting groove 2111. The inner diameter of the first mounting groove 2111 is larger than the outer diameters of the magnet 223 and the flywheel 222 to prevent the magnet 223 and the flywheel 222 from touching the inner wall of the first mounting groove 2111 when rotating. The first limiting groove 2112 is configured for accommodating the distal bearing 24 and the distal bearing 24 is fixed in the first limiting groove 2112. The distal bearing 24 is in contact with the side wall of the first limiting groove 2112 to prevent the distal bearing 24 from moving in the radial direction. Referring to FIG. 6, the rotating shaft 221 is provided with a distal limiting portion 2211, and the distal limiting portion 2211 cooperates with the bottom wall of the first limiting groove 2112 to limit the distal bearing 24 between the distal limiting portion 2211 and the first limiting groove 2112 to prevent the distal bearing 24 from moving in the axial direction. The through hole 2113 is configured for the distal end of the rotating shaft 221 to pass through. The through hole 2113 is in clearance fit with the rotating shaft 221, and the distal end of the rotating shaft 221 extends to the outside of the casing 21 through the through hole 2113 and is fixedly connected to the impeller 10.

Figure 10:
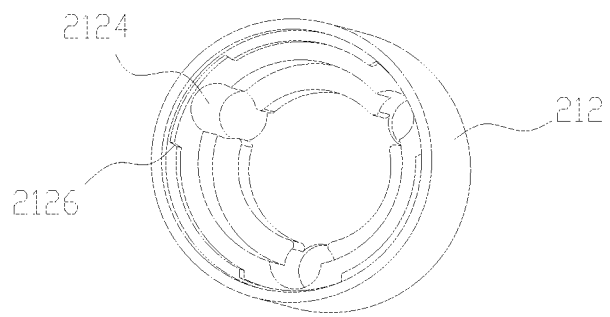
FIG. 10 is a schematic structural view of a second housing of the casing shown in FIG. 9.

Referring to FIG. 9 and FIG. 10, the second casing 212 is generally provided with an open end at one end and a closed end at the other end. Along the direction from the distal end to the proximal end of the second casing 212, the second casing 212 is provided with a second connecting groove 2120, a second mounting groove 2121, a second limiting groove 2122, a third limiting groove 2123 and a connection hole 2124. The second connecting groove 2120 is configured for connecting with the third casing 213. During assembly, the proximal connection member 2132 of the third casing 213 is inserted into the second connecting groove 2110, so that the second casing 212 and the third casing 213 are fixedly connected. The second mounting groove 2121 is configured for accommodating the back plate 233, and the back plate 233 is fixed in the second mounting groove 2121. The side wall of the second mounting groove 2121 is provided with engagement grooves 2126, and the engagement grooves 2126 are recessed from the side wall of the second mounting groove 2121 toward the outer surface of the second casing 212. Referring to FIG. 8, the side wall of the back plate 233 is provided with limiting protrusions 2334. During assembly, the limiting protrusions 2334 of the back plate 233 are pressed against the engagement grooves 2126 to prevent the back plate 233 from rotating in the second mounting groove 2121.

The second limiting groove 2122 is configured for accommodating the control member 26, and the control member 26 is fixed in the second limiting groove 2122. In this embodiment, the control member 26 includes two PCB boards superimposed in the axial direction, and the connection wires of the coil winding 232 are respectively connected to the corresponding PCB boards. Each PCB is provided with a second mounting hole, the second mounting hole is in clearance fit with the rotating shaft 221, and the rotating shaft 221 rotatably passes through the second mounting hole. It can be understood that this embodiment does not limit the specific number of PCB boards, and one, three or more PCB boards may be provided as required.

The third limiting groove 2123 is configured for accommodating the proximal bearing 25 and the proximal bearing 25 is fixed in the third limiting groove 2123. The proximal bearing 25 is in contact with the side wall of the third limiting groove 2123 to prevent the proximal bearing 25 from moving in the radial direction. As shown in FIG. 6, the rotating shaft 221 is provided with a proximal limiting portion 2212, and the proximal limiting portion 2212 cooperates with the bottom wall of the third limiting groove 2123 to limit the proximal bearing 25 between the proximal limiting portion 2212 and the third limiting groove 2123 to prevent the proximal bearing 25 from moving in the axial direction.

The connection holes 2124 are configured for passing the supply pipelines (eg, cleaning pipelines, and wires electrically connected to the PCB board) in the catheter 40. In the embodiment shown in FIG. 10, there are three connection holes 2124, and each connection hole 2124 penetrates through the second casing 212 in the axial direction.

Referring specifically to FIG. 9, the third casing 213 is generally a structure with two ends open, and the third casing 213 is sleeved outside the stator 23. Two ends of the third casing 213 are respectively provided with a distal connection member 2131 and a proximal connection member 2132. During assembly, the distal connection member 2131 is inserted into the first connecting groove 2110 of the first casing 211, and the proximal connection member 2132 is inserted into the second connecting groove 2120 of the second casing 212 respectively.

It can be understood that the casing 21 in this embodiment is only used as an example, and does not limit the present application. The casing 21 of the present application can also be of other structures, as long as it can be sleeved outside the stator 23 and the rotor 22 to seal the stator 23 and the rotor 22. For example, in other embodiments, the casing 21 includes a first casing 211 sleeved outside the distal end of the rotor 22, a second casing 212 sleeved outside the proximal end of the rotor 22, and a stator 23 sleeved outside the third casing 213. The third casing 213 and the second casing 212 are integrally formed, or the third casing 213 and the first casing 211 are integrally formed.

Figure 11:
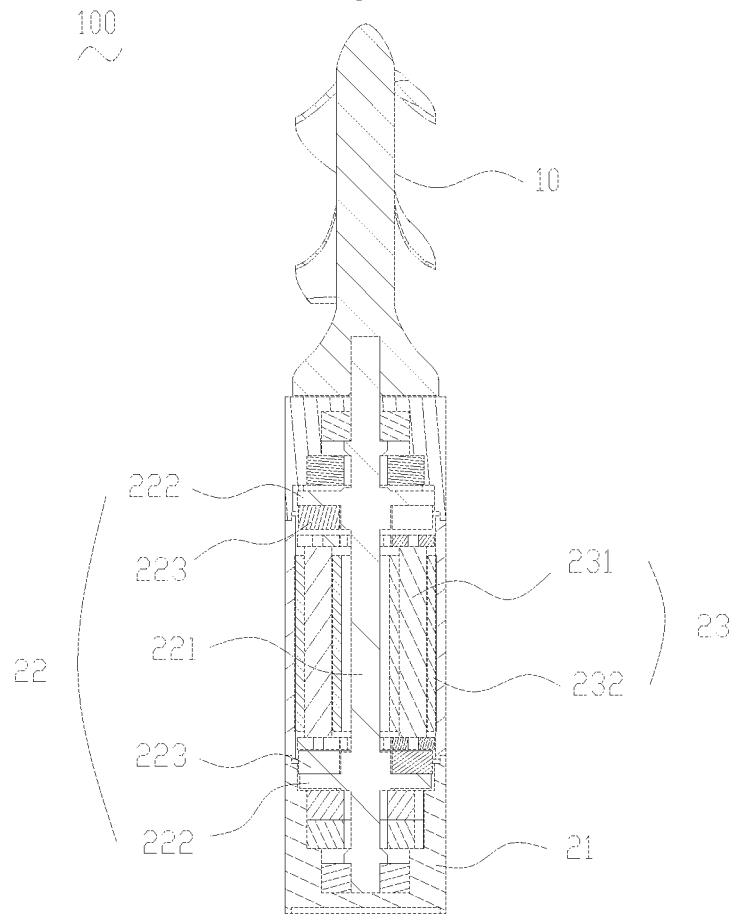
FIG. 11 is a cross-sectional view of an impeller and a drive unit of a blood pump provided by a second embodiment of the present application.
Figure 12:
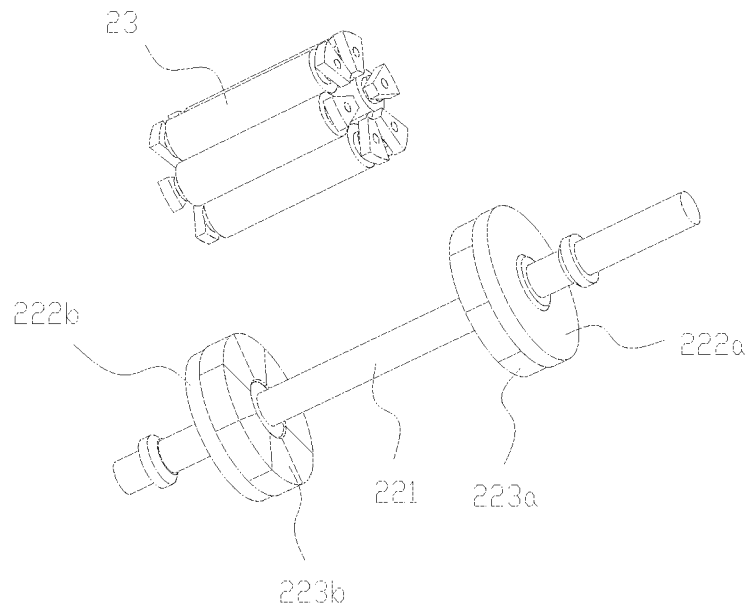
FIG. 12 is an exploded view of a stator and a rotor of the drive unit shown in FIG. 11.

Referring to FIG. 11 and FIG. 12, a second embodiment of the present application provides a blood pump 100. The blood pump 100 includes an impeller 10, a drive unit, a cannula, and a catheter. The drive unit includes a casing 21, and a rotor 22 and a stator 23 arranged in the casing 21. The rotor 22 includes a rotating shaft 221, and the rotating shaft 221 extends to the outside of the casing 21 and is connected to the impeller 10.

The difference between the second embodiment and the blood pump of the first embodiment is that the rotor 22 has two magnets 223, which are a first magnet 223a and a second magnet 223b respectively, and the first magnet 223a and the second magnet 223b are arranged along the axis of the rotating shaft 221 at intervals, the stator 23 is located between the first magnet 223a and the second magnet 223b, and the rotating magnetic field generated by the stator 23 are respectively interacted with the first magnet 223a and the second magnet 223b, so as to rotate the rotating shaft 221. Correspondingly, the rotor 22 also has two flywheels 222 disposed on the rotating shaft 221 along the axial direction at intervals, which are a first flywheel 222a and a second flywheel 222b respectively. The first magnet 223a is mounted on the first flywheel 222a, and the second magnet 223b is mounted on the second flywheel 222b.

Figure 13:
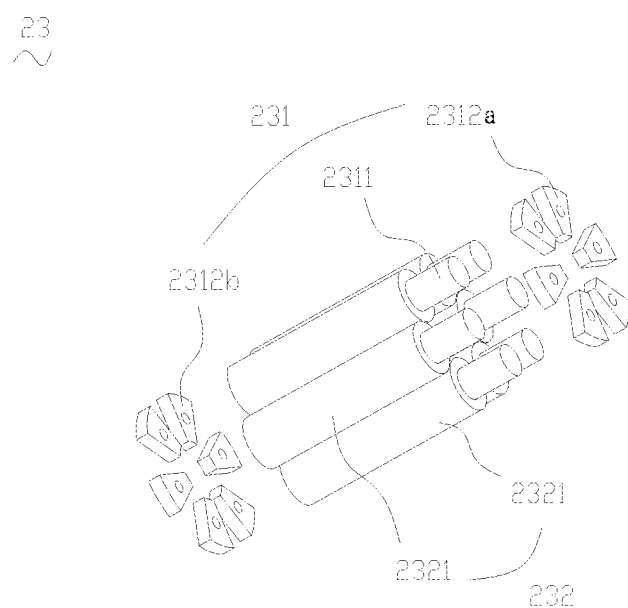
FIG. 13 is an exploded view of the stator shown in FIG. 12.

Referring to FIG. 13, the stator 23 includes a plurality of posts 231 arranged around the axis of the rotating shaft 221, and coil winding 232 surrounding the peripheries of the posts 231. The rotating magnetic fields generated by the coil winding 232 are mutually connected to the first magnet 223a and the second magnet 223b respectively, so as to rotate the rotating shaft 221.

Compared with the first embodiment, the rotor 22 of the second embodiment includes two magnets 223, and the rotating magnetic field generated by the stator 23 interacts with the two magnets 223 respectively, and the two magnets 223 drive the rotating shaft 221 to rotate, which can greatly increase the speed of the rotating shaft 221 and increase the output power and load torque of the drive unit. In addition, the stator 23 and the two magnet 223 is arranged at intervals along the axial direction, and the rotating shaft 221 is driven to rotate by the direct drive of the axial magnetic flux, which can increase the output power and load torque of the drive unit 20 without increasing the overall radial size of the drive unit 20.

The structure of the drive unit 20 of the blood pump 100 of the second embodiment will be described in detail as follows.

Figure 14:
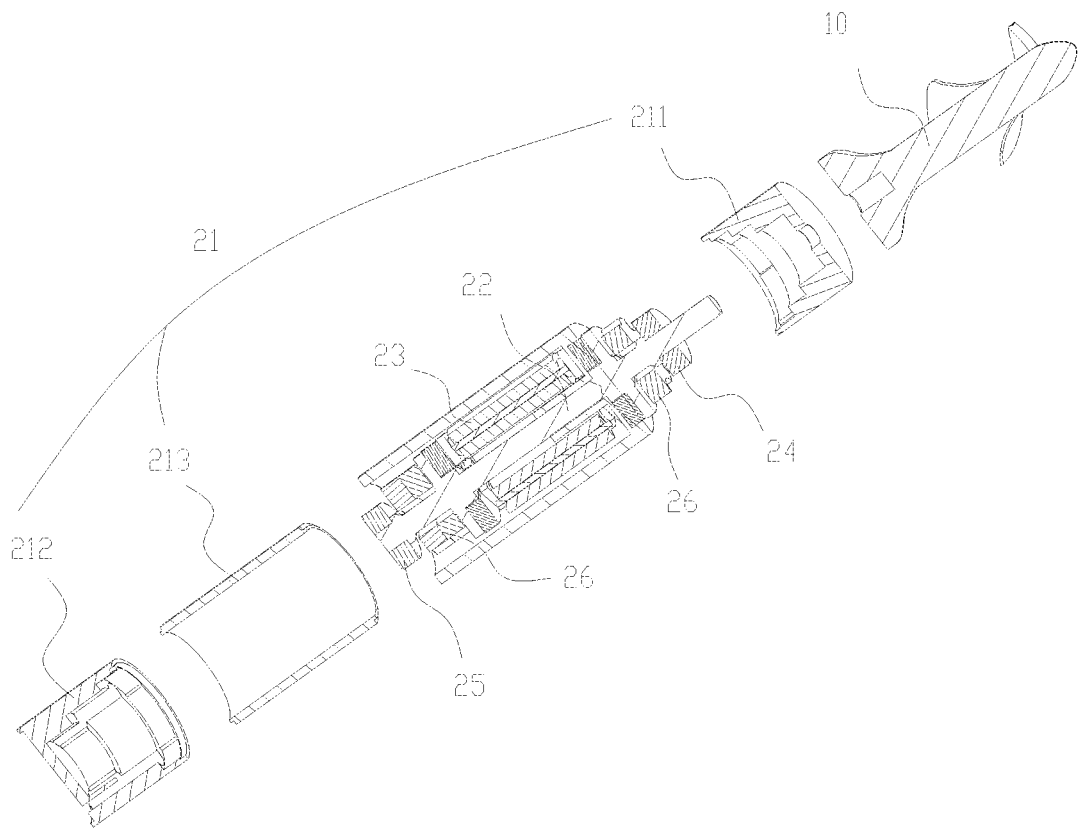
FIG. 14 is an exploded view of the impeller and drive unit shown in FIG. 11.

Referring to FIG. 14, the drive unit 20 includes a casing 21, a rotor 22, and a stator 23, a distal bearing 24, a proximal bearing 25 and a control member 26 respectively mounted in the casing 21. Further referring to FIG. 12, the rotor 22 includes a rotating shaft 221, a first flywheel 222a, a second flywheel 222b, a first magnet 223a and a second magnet 223b. The distal end of the rotating shaft 221 extends out of the casing 21 and is fixedly connected with the impeller 10. The first flywheel 222a and the second flywheel 222b are disposed on the rotating shaft 221 along an axial direction at intervals, and the stator 23 is located between the first flywheel 222a and the second flywheel 222b. The first magnet 233a is fixed on the side of the first flywheel 222a close to the stator 23, and the second magnet 233b is fixed on the side of the second flywheel 222b close to the stator 23. The specific structures of the magnets and the flywheels of the rotor 22 of the second embodiment are the same as those of the magnet and the flywheel of the first embodiment, and will not be repeated here. Referring again to FIG. 13, the stator 23 includes a plurality of posts 231 arranged around the axis of the rotating shaft 221, and coil winding 232 surrounding the peripheries of the posts 231. The center of the stator 23 has a passage penetrating in the axial direction, and the rotating shaft 221 rotatably passes through the passage.

Compared with the first embodiment, the stator 23 of the second embodiment exclude a back plate, and each post 231 includes a rod portion 2311, and a first head portion 2312a and a second head portion 2312b respectively disposed at both ends of the rod portion 2311. The first head portion 2312a is opposite to the first magnet 223a, and the second head portion 2312b is opposite to the second magnet 223b. The posts 231 serve as magnetic core, which is made of soft magnetic material, such as cobalt steel or the like. The axial distance between the first magnet 223a and the posts 231 is ranged from 0.1 mm to 2 mm, for example, 0.1 mm to 0.5 mm; the axial distance between the second magnet 223b and the posts 231 is ranged from 0.1 mm to 2 mm, for example, 0.1 mm to 0.5 mm. The coil winding 232 includes a plurality of coils 2321. The number of the coils 2321 is the same as the number of the posts 231. The periphery of each rod portion 2311 is surrounded by the coils 2321. The coil winding 232 is sequentially controlled by a control unit (not shown) to create a rotating magnetic field for driving the two magnets.

Figure 15:
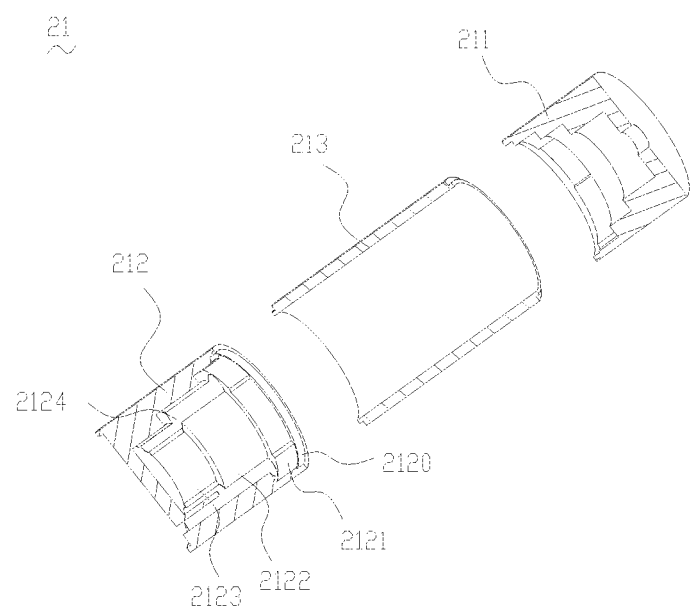
FIG. 15 is an exploded view of a casing of the drive unit shown in FIG. 11.

Referring to FIG. 15, the casing 21 includes a first casing 211, a second casing 212 and a third casing 213. The first casing 211 is sleeved outside the distal end of the rotor 22, the second casing 212 is sleeved outside the proximal end of the rotor 22, and the third casing 213 is sleeved outside the stator 23. Since the structures of the first casing 211 and the third casing 213 of the second embodiment are the same as those of the first embodiment, the specific structures of the first casing 2112 and the third casing 213 will not be repeated here.

The second casing 212 is generally a structure provided with one open end and a closed end. Along the direction from the distal end to the proximal end of the second casing 212, the second casing 212 is provided with a second connecting groove 2120, a second mounting groove 2121, a second limiting groove 2122, a third limiting groove 2123 and connection holes. The second mounting groove 2121 is configured for accommodating the second flywheel 222b and the second magnet 223b, and the second flywheel 222b and the second magnet 223b are rotatably accommodated in the second accommodating groove. The inner diameter of the second mounting groove 2121 is larger than the outer diameter of the second flywheel 222b and the second magnet 223b to prevent the second flywheel 222b and the second magnet 223b from touching the inner wall of the second mounting groove 2121 when rotating.

Similar to the first embodiment, the second connecting groove 2120 is configured for connecting with the third casing 213. The second limiting groove 2122 is configured for accommodating the control member 26, and the control member 26 is fixed in the second limiting groove 2122. The third limiting groove 2123 is configured for accommodating the proximal bearing 25 and the proximal bearing 25 is fixed in the third limiting groove 2123. The connection holes are used for supply pipelines (eg, cleaning pipelines, and wires electrically connected to the PCB board) in the catheter 40 to pass through, and the connection holes penetrate through the second casing 212 in the axial direction.

Figure 16:
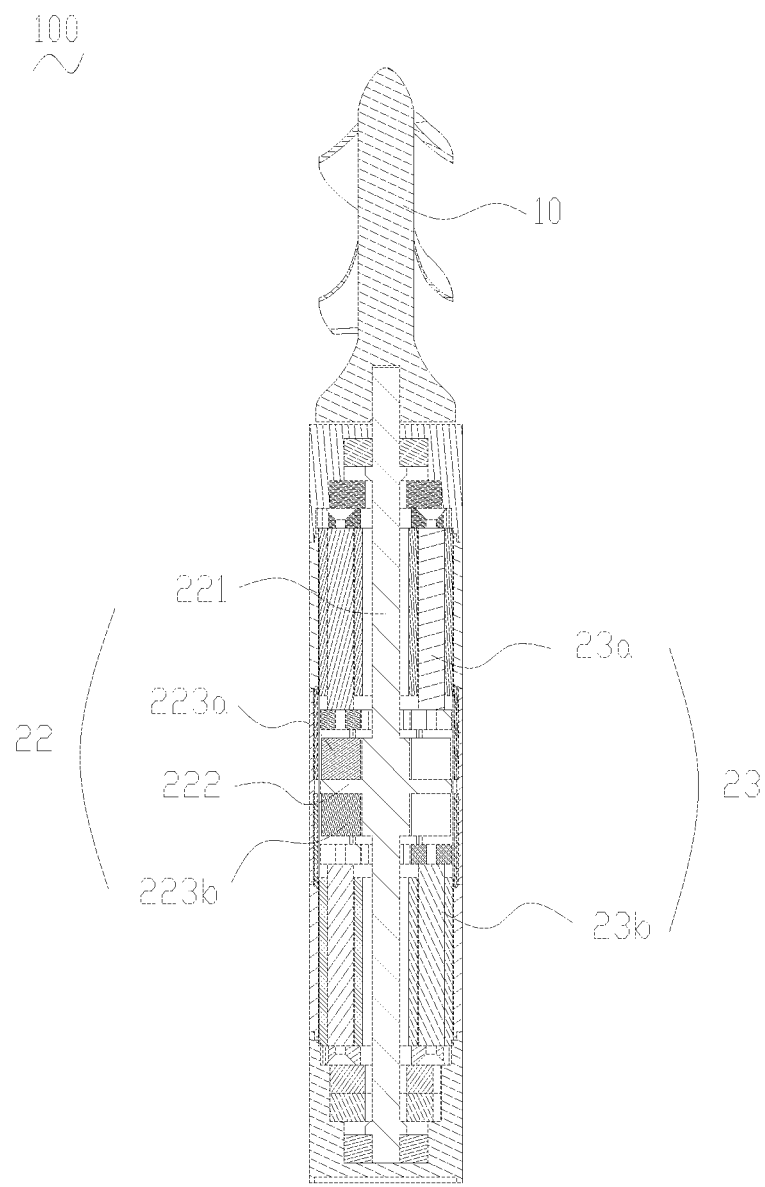
FIG. 16 is a cross-sectional view of an impeller and a drive unit of a blood pump provided by the third embodiment of the present application.
Figure 17:
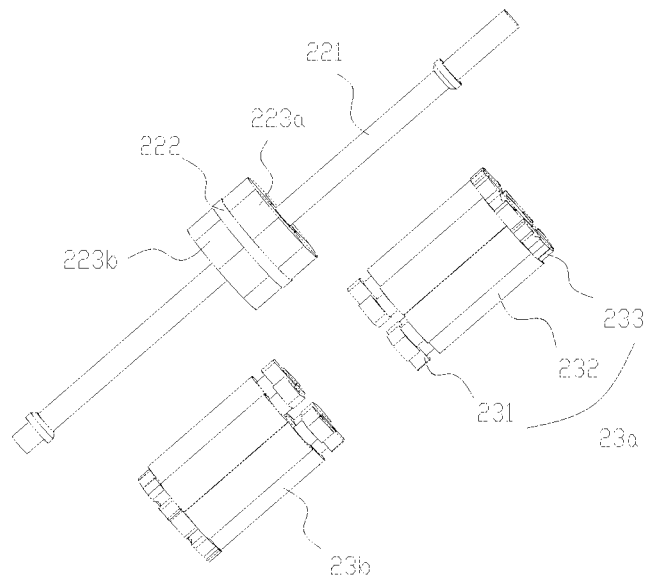
FIG. 17 is an exploded view of a stator and a rotor of the drive unit shown in FIG. 16.

Referring to FIG. 16 and FIG. 17, a third embodiment of the present application provides a blood pump 100. The blood pump 100 includes an impeller 10, a drive unit, a cannula, and a catheter. The drive unit includes a casing 21, and a rotor 22 and a stator 23 arranged in the casing 21. The rotor 22 includes a rotating shaft 221, and the rotating shaft 221 extends to the outside of the casing 21 and is connected to the impeller 10.

The difference between the third embodiment and the first embodiment is that the rotor 22 has two magnets, which are the first magnet 223a and the second magnet 223b, and the first magnet 223a and the second magnet 223b are arranged at intervals along the axis of the rotating shaft 221, there are two stators 23, which are the first stator 23a and the second stator 23b, the first stator 23a and the second stator 23b are arranged at intervals along the axis of the rotating shaft 221, and the rotating magnetic field generated by the first stator 23a capable of interacting with the first magnet 223 at to rotate the rotating shaft 221, and the rotating magnetic field generated by the second stator 23b capable of interacting with the second magnet 223b to rotate the rotating shaft 221.

Specifically, the first stator 23a and the second stator 23b are located between the first magnet 223a and the second magnet 223b. More specifically, the flywheel 222 of the rotor 22 is located between the first stator 23a and the second stator 23b, and the first magnet 223a and the second magnet 223b are respectively fixed on the flywheel 222. The first stator 23a and the second stator 23b have the same structure, and both include a plurality of posts 231 and coil winding 232 surrounding the peripheries of the posts 231. The rotating magnetic fields generated by the coil windings 232 of the two stators 23 interact with the corresponding magnets to rotate the rotating shaft 221. The axial distance between the posts 231 of the first stator 23a and the first magnet 223a is ranged from 0.1 mm to 2 mm, for example, 0.1 mm to 0.5 mm; the axial distance between the posts 231 of the second stator 23b and the second magnet 223b is ranged from 0.1 mm to 2 mm, for example, 0.1 mm to 0.5 mm.

Compared with the first embodiment, the drive unit 20 of the third embodiment has two stators 23, and the two stators 23 interact with corresponding magnets respectively, so that the two stators 23 simultaneously drive the two magnets fixed to the rotating shaft 221 to rotate, thereby greatly increasing the rotational speed of the rotating shaft 221 and increasing the output power and load torque of the drive unit 20. Moreover, the two stators 23 are arranged on the rotating shaft 221 in the axial direction, and the radial size of the drive unit 20 will not be increased. That is, the present embodiment can greatly increase the output power and load torque of the drive unit 20 without increasing the overall radial size of the drive unit 20.

The structure of the drive unit 20 will be specifically described below.

Figure 18:
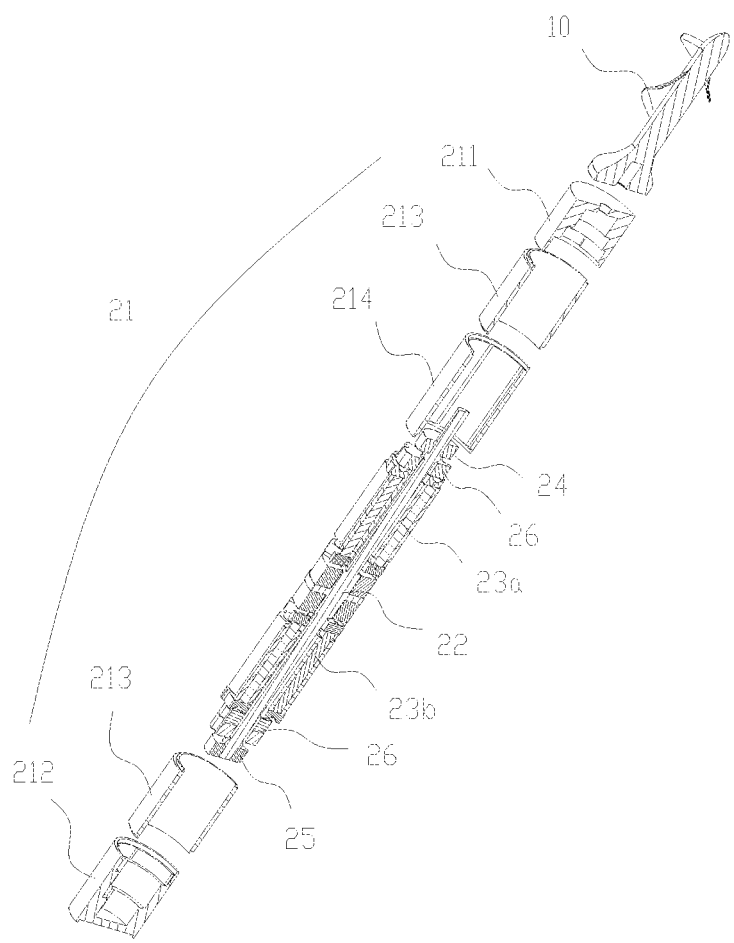
FIG. 18 is an exploded view of the impeller and drive unit shown in FIG. 16.
Figure 19:
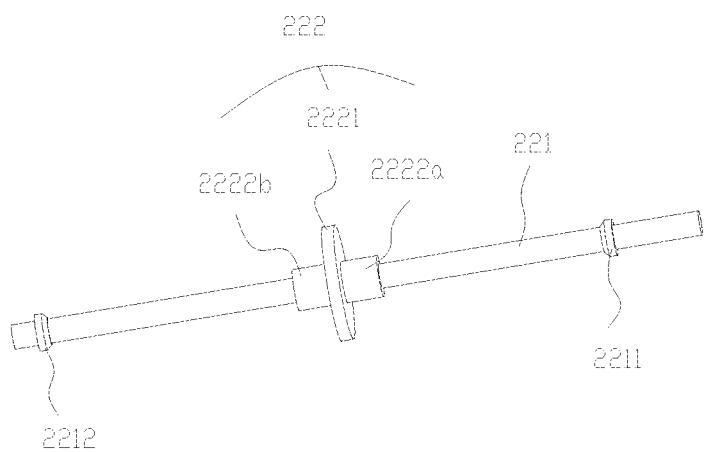
FIG. 19 is a schematic structural view of a rotating shaft and a flywheel of the rotor shown in FIG. 17.

Referring to FIG. 18, the drive unit 20 includes a casing 21, and a rotor 22, a first stator 23a, a second stator 23b, a distal bearing 24, a proximal bearing 25 and a control member 26 respectively mounted in the casing 21, The rotor 22 includes a rotating shaft 221, a flywheel 222, a first magnet 223a and a second magnet 223b. Referring to FIG. 19, the flywheel 222 includes a body portion 2221, a first mounting boss 2222a and a second mounting boss 2222b. The body portion 2221 is generally a disk-shaped structure, such as a disc structure, which is fixed on the rotating shaft 221. The first mounting boss 2222a and the second mounting boss 2222b are respectively arranged on both sides of the body portion 2221 in the axial direction. The first magnet 223a is arranged around the periphery of the first mounting boss 2222a, and the second magnet 223b is arranged around the periphery of the second mounting boss 2222b. The structures of the two magnets of the third embodiment are the same as the structures of the magnet of the first embodiment, and are not repeated here.

Likewise, the structure of each stator 23 of the third embodiment is the same as that of the stator of the first embodiment, including a plurality of posts 231 arranged around the axis of the rotating shaft 221, coil winding 232 surrounding the peripheries of the posts 231, and a back plate 233. Therefore, the specific structures of the two stators are not repeated here. The back plate 233 of the first stator 23a is connected to the end of the posts 231 of the first stator 23a away from the first magnet 223a, and the back plate 233 of the second stator 23b is connected to the end of the posts 231 of the second stator 23b away from the second magnet 223b.

Figure 20:
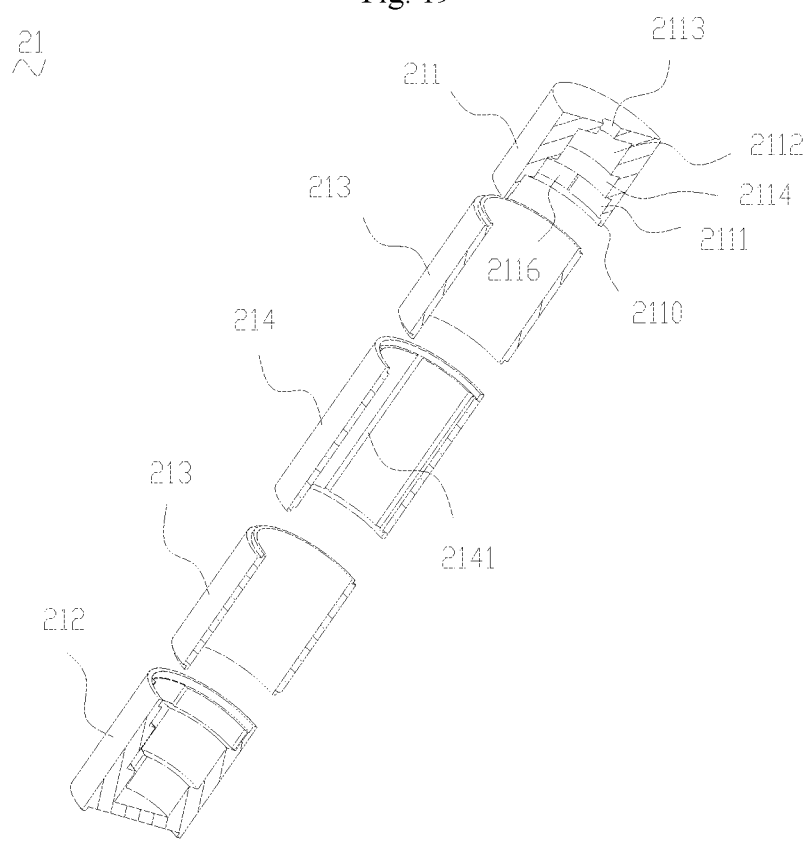
FIG. 20 is an exploded view of a casing of the drive unit shown in FIG. 16.

Referring to FIG. 20, the casing 21 includes a first casing 211, a second casing 212, two third casings 213 and a fourth casing 214. The first casing 211 is sleeved outside the distal end of the rotor 22, the second casing 212 is sleeved outside the proximal end of the rotor 22, the two third casings 213 are sleeved outside the two stators 23 respectively, and the fourth casing 214 is located between the two third casings 213 and is sleeved outside the flywheel 222. Since the structures of the second casing 212 and the third casing 213 of the third embodiment are the same as those of the first embodiment, the specific structures of the second casing 212 and the third casing 213 will not be repeated here.

The first casing 211 is generally a structure provided with an open end and a closed end. Along the direction from the proximal end to the distal end of the first casing 211, the first casing 211 is provided with a first connecting groove 2110, a first mounting groove 2111, a first limiting groove 2112, a fourth limiting groove 2114, and a through hole 2114 that communicate with each other. The first mounting groove 2111 is configured accommodating the back plate 233 of the first stator 23a, and the back plate 233 is fixed in the first mounting groove 2111. The side wall of the first mounting groove 2111 is provided with a positioning groove 2116, and the positioning groove 2116 is recessed from the side wall of the first mounting groove 2111 toward the outer surface of the first casing 211. Referring to FIG. 8, the side wall of the back plate 233 is provided with a limiting protrusion 2334. During assembly, the limiting protrusion 2334 of the back plate 233 is pressed against the positioning groove 2116 to prevent the back plate 233 from rotating in the first mounting groove 2111. The fourth limiting groove 2114 is used for accommodating the control member 26, and the control member 26 is fixed in the fourth limiting groove 2114. In the embodiment, the control member 26 includes three PCB boards, and the connection wires of the coil winding 232 are respectively connected to the corresponding PCB boards. Among them, one PCB board is fixed in the fourth limiting groove 2114 of the first casing 211, and the other two PCB boards are superposed and fixed in the second casing 212 in the axial direction. It can be understood that this embodiment does not limit the specific number of PCB boards, and one, four or more PCB boards can be provided as required.

Same as the first embodiment, the first connecting groove 2110 is configured for connecting with the third casing 213. The first limiting groove 2112 is configured for accommodating the distal bearing 24, and the distal bearing 24 is fixed in the first limiting groove 2112. The through hole 2113 is configured for the distal end of the rotating shaft 221 to pass through, and the distal end of the rotating shaft 221 extends to the outside of the casing 21 through the through hole 2113 and is fixedly connected to the impeller 10. The fourth casing 214 is generally a structure with two ends open, and is sleeved outside the flywheel 222. Two ends of the fourth casing 214 are respectively provided with connection members matched with the third casing 213, so that the fourth casing 214 is fixedly connected with the third casings 213 located on both sides of the fourth casing 214. The inner wall of the fourth casing 214 is provided with a positioning structure 2141, and the connection wires of the coil winding 232 is fixed in the positioning structure 2141. By fixing the connection wires of the coil winding 232 on the positioning structure 2141, the connection wires of the coil winding 232 can be kept away from the flywheel 222, and at the same time, the connection wires can be prevented from moving freely, thereby preventing the flywheel 222 from damaging the connection wires when the flywheel 222 rotates at a high speed.

In the embodiment shown in FIG. 20, the positioning structure 2141 is a groove structure extending in the axial direction, and the connection wires of the coil winding 232 are clamped in the groove structure to prevent the connection wires from moving freely. It can be understood that the present embodiment does not limit the specific structure of the positioning structure 2141, as long as it can prevent the connection wires of the coil winding 232 from being damaged by the flywheel 222. For example, in other embodiments, the positioning structure 2141 is two hole structures arranged at intervals, and the connection wires of the coil winding 232 extend to the outside of the fourth casing 214 through one of the hole structures, another hole structure extends into the fourth casing 214.

It can be understood that the casing 21 in this embodiment is only used as an example, and does not limit the present application. The casing 21 of the present application can also be of other structures, as long as it can be sleeved outside the stator 23 and the rotor 22 to seal the stator 23 and the rotor 22. For example, in other embodiments, the casing 21 includes a first casing 211 sleeved outside the distal end of the rotor 22, a second casing 212 sleeved outside the proximal end of the rotor 22, and a fifth casing sleeved outside two stators and the flywheel.

Figure 21:
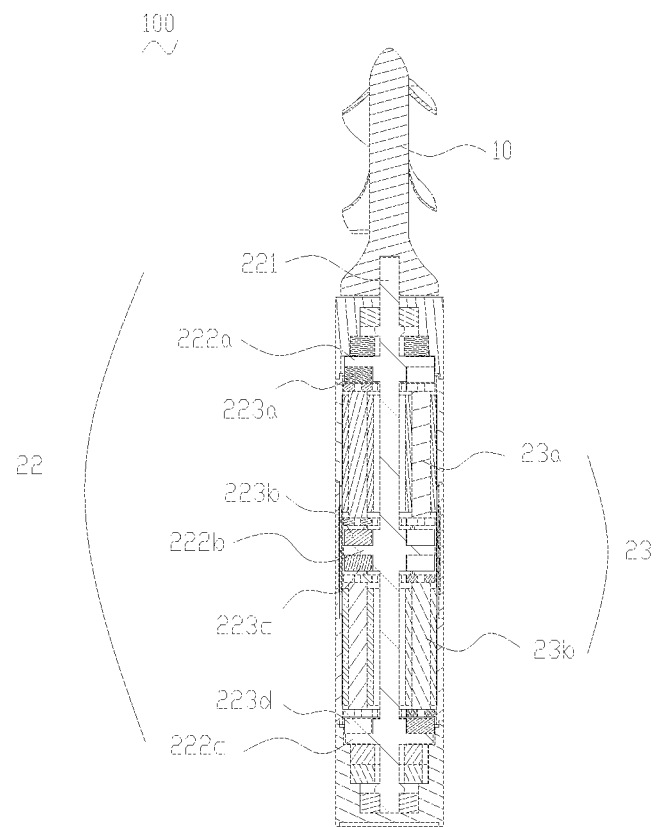
FIG. 21 is a cross-sectional view of an impeller and a drive unit of a blood pump provided by the fourth embodiment of the present application.
Figure 22:
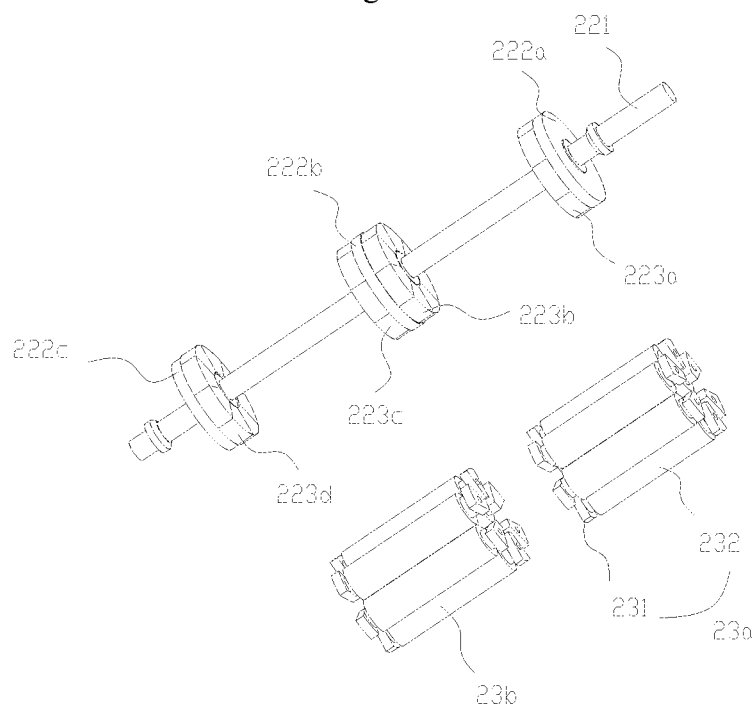
FIG. 22 is an exploded view of a rotor and a stator of the drive unit shown in FIG. 21.

Referring to FIG. 21 and FIG. 22, a fourth embodiment of the present application provides a blood pump 100. The blood pump 100 includes an impeller 10, a drive unit 20, a cannula and a catheter. The drive unit includes a casing 21, and a rotor 22 and a stator 23 arranged in the casing 21. The rotor 22 includes a rotating shaft 221, and the rotating shaft 221 extends to the outside of the casing 21 and is connected to the impeller 10.

The fourth embodiment differs from the second embodiment in that the rotor 22 has four magnets, which are a first magnet 223a, a second magnet 223b, a third magnet 223c and a fourth magnet 223d, respectively. There are two stators 23, which are a first stator 23a and a second stator 23b, respectively. The first stator 23a is located between the first magnet 223a and the second magnet 223b, and the rotating magnetic field generated by the first stator 23a capable of interacting with the first magnet 223a and the second magnet 223b respectively to rotate the rotating shaft 221. The second stator 23b is located between the third magnet 223c and the fourth magnet 223d, and the rotating magnetic field generated by the second stator 23b interacts with the third magnet 223c and the fourth magnet 223d to rotate the shaft 221 respectively. Correspondingly, the rotor 22 has three flywheels, which are a first flywheel 222a, a second flywheel 222b and a third flywheel 222c. The first flywheel 222a, the second flywheel 222b and the third flywheel 222c are arranged on the rotating shaft 221 at intervals along the axis of the rotating shaft 221, the first flywheel 222a is fitted with a first magnet 223a, the second flywheel 222b is fitted with a second magnet 223b and a third magnet 223c respectively, and the third flywheel 222c is fitted with a fourth magnet 223d.

Figure 23:
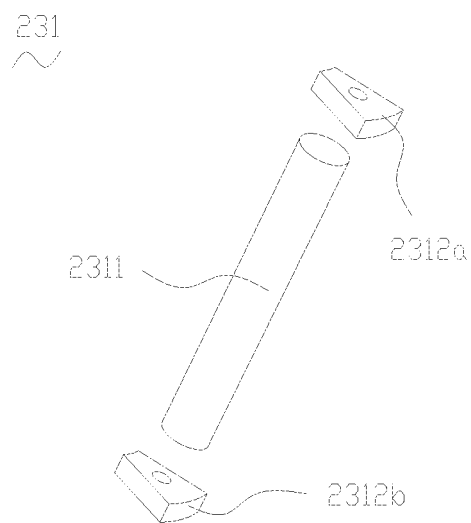
FIG. 23 is an exploded view of a post of the stator shown in FIG. 22.
Figure 24:
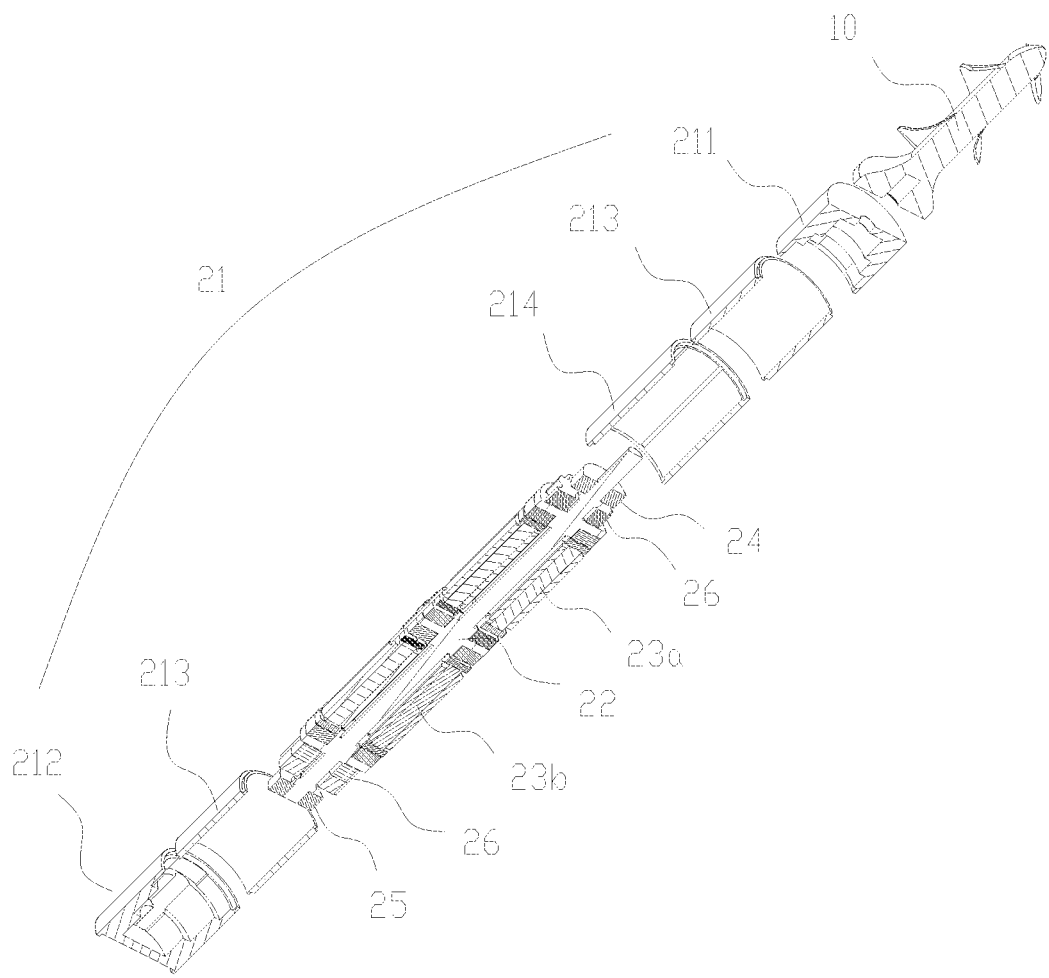
FIG. 24 is an exploded view of the impeller and drive unit shown in FIG. 21.

Specifically, each stator 23 includes a plurality of posts 231 arranged around the axis of the rotating shaft 221, and coil winding 232 surrounding the peripheries of the posts 231. As shown in FIG. 23, each post 231 includes a rod portion 2311, and a first head portion 2312a and a second head portion 231 b respectively disposed at both ends of the rod portion 2311. The axial distance between the posts 231 of the first stator 23a and the first magnet 223a or/and the second magnet 223b is ranged from 0.1 mm to 2 mm, for example, 0.1 mm to 0.5 mm. The axial distance between the posts 231 of the second stator 23b and the third magnet 223c or/and the fourth magnet 223d is ranged from 0.1 mm to 2 mm, for example, 0.1 mm to 0.5 mm.

Compared with the second embodiment, the fourth embodiment uses two stators 23 to drive four magnets to drive three flywheels 222 to rotate, which can greatly increase the output power and load torque of the drive unit 20. In addition, the two stators 23 are arranged at intervals in the axial direction, and the flywheels 222 are driven to rotate by the direct drive of the axial magnetic flux, which can increase the output power and load rotation of the drive unit 20 without increasing the overall radial size of the drive unit 20.

Since each stator 23 of the fourth embodiment has the same structure as that of the second embodiment, the specific structure of the stator 23 will not be repeated here. Likewise, since the structure of the casing 21 of the fourth embodiment is the same as that of the third embodiment, the specific structure of the casing 21 will not be repeated here.

Figure 25:
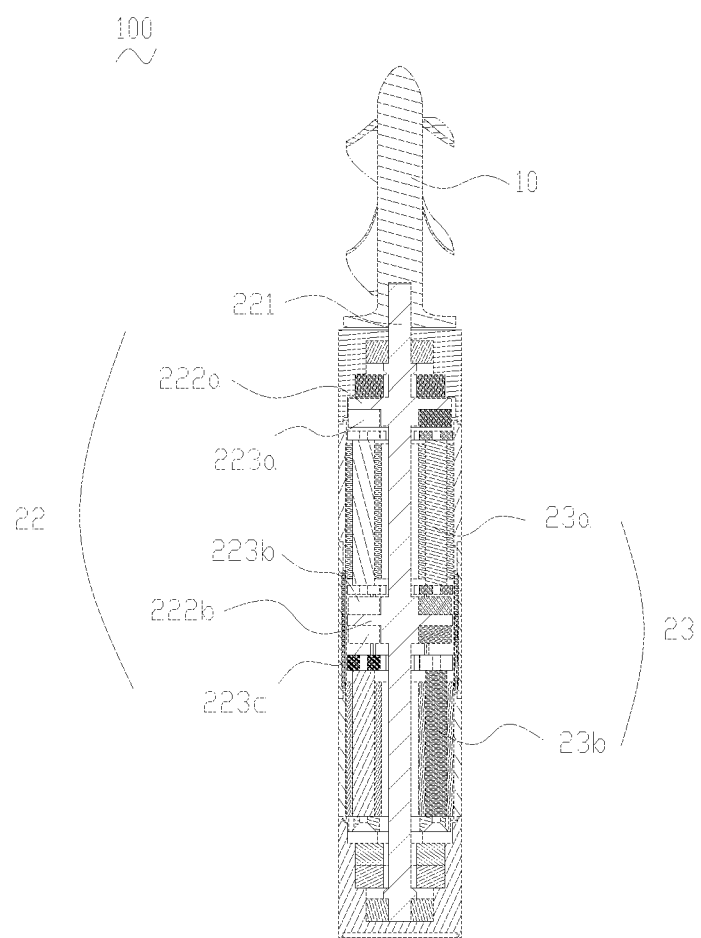
FIG. 25 is a cross-sectional view of an impeller and a drive unit of a blood pump provided by the fifth embodiment of the present application.
Figure 26:
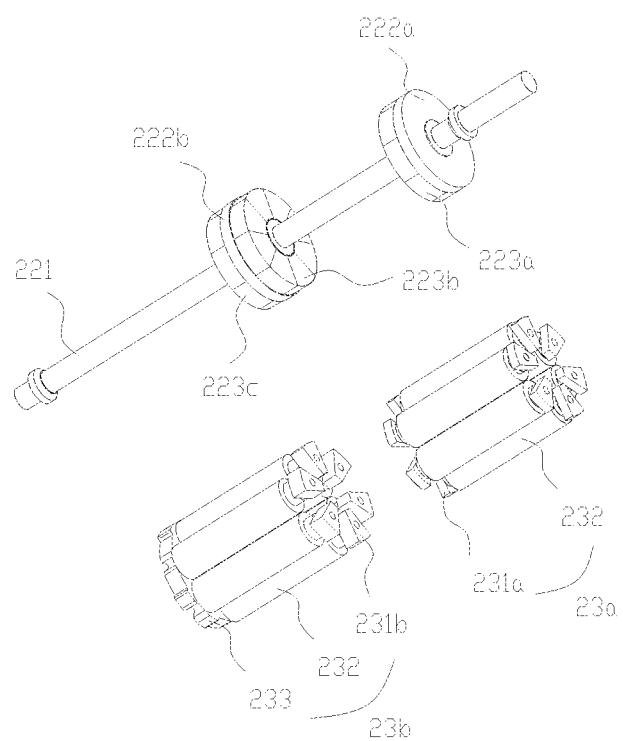
FIG. 26 is an exploded view of a rotor and a stator of the drive unit shown in FIG. 25.

Referring to FIG. 25 and FIG. 26, a fifth embodiment of the present application provides a blood pump 100. The blood pump 100 includes an impeller 10, a drive unit 20, a cannula, and a catheter. The drive unit includes a casing 21, and a rotor 22 and a stator 23 arranged in the casing 21. The rotor 22 includes a rotating shaft 221, and the rotating shaft 221 extends to the outside of the casing 21 and is connected to the impeller 10.

The fifth embodiment differs from the second embodiment in that the rotor 22 has three magnets, two first magnets 223a and 223b, and one second magnet 223c. The two first magnets 223a and 223b, the one second magnet 223c are disposed on the rotating shaft 221 at intervals along the axis of the rotating shaft 221. There are two stators 23, which are a first stator 23a and a second stator 23b, respectively. The first stator 23a and the second stator 23b are arranged at intervals along the rotating shaft 221. The first stator 23a is located between the first magnet 223a and 223b, and the rotating magnetic field generated by the first stator 23a interacts with the first magnet 223a and 223b respectively to rotate the shaft 221; the second stator 23b is arranged opposite to the second magnet 223c, the rotating magnetic field generated by the second stator 23b interacts with the second magnet 223c to rotate the shaft 221. Correspondingly, the rotor 22 includes two flywheels disposed on the rotating shaft 221 at intervals along the axis of the rotating shaft 221, which are a first flywheel 222a and a second flywheel 222b respectively. The first flywheel 222a is fitted with the first magnet 223a, and the second flywheel 222b is fitted with first magnet 223b and a second magnet 223c.

Specifically, the first stator 23a includes a plurality of first posts 231a arranged around the axis of the rotating shaft 221, and coil winding 232 surrounding the peripheries of the first posts 231a. Each first post 231a includes a rod portion, a first head portion, and a second head portion respectively disposed at both ends of the rod portion. The second stator 23b includes a plurality of second posts 231 b arranged around the axis of the rotating shaft 221, coil winding 232 surrounding the peripheries of the second posts 231b, and a back plate 233. Each second post 231b includes a rod portion, and a head portion connected to one end of the rod portion, and the back plate 233 is connected to an end of the rod portion 2311 away from the head portion. The axial distance between the first posts 231a and the first magnet 223a or/and the second magnet 223b is ranged from 0.1 mm to 2 mm, for example, 0.1 mm-0.5 mm. The axial distance between the second posts 231b and the third magnet 223c is ranged from 0.1 mm to 2 mm, for example, 0.1 mm-0.5 mm.

Compared with the second embodiment, the fifth embodiment uses two stators 23 to drive three magnets to drive two flywheels 222 to rotate, which can greatly increase the output power and load torque of the drive unit 20. In addition, the two stators 23 are arranged at intervals along the axial direction, and the flywheels 222 are driven to rotate by the direct drive of the axial magnetic flux, which can increase the output power and load rotation of the drive unit 20 without increasing the overall radial size of the drive unit 20.

Since the structure of the first stator 23a of the fifth embodiment is the same as that of the second embodiment, the structure of the second stator 23b is the same as that of the first embodiment, and the first stator 23a and the second stator 23b have the same structure. The specific structure is not repeated here. Likewise, since the structure of the casing 21 of the fifth embodiment is the same as that of the third embodiment, the specific structure of the casing 21 will not be repeated here.

It can be understood that, without prejudice to the purpose of the present application, the free combination of the technical solutions in each embodiment to form a new technical solution is also the scope of the protection to be applied for in the present application. Those skilled in the art can clearly understand that, for the convenience and brevity of description, the specific working process of the above-described systems, devices and units may refer to the corresponding processes in the foregoing method embodiments, which will not be repeated here.

The above are only optional embodiments of the present application, and are not intended to limit the present application. Various modifications and variations of the present application are possible for those skilled in the art. Any modification, equivalent replacement, improvement, etc. made within the spirit and principle of the present application shall be included within the scope of the claims of the present application.

What is claimed is:

1. A blood pump, comprising:
   a cannula, provided with a blood flow inlet and a blood flow outlet;
   an impeller, disposed in the cannula; and
   a drive unit, capable of driving the impeller to rotate and comprising:
   a casing, connected to the cannula;
   a rotor, comprising a rotating shaft and a magnet, wherein the rotating shaft is partially accommodated in the casing, and partially extends to an outside of the casing and is connected with the impeller; the magnet is accommodated in the casing and arranged on the rotating shaft; and
   a stator, comprising a plurality of posts arranged around an axis of the rotating shaft, and a coil winding around peripheries of the posts, wherein the coil winding capable of generating a rotating magnetic field that interacts with the magnet to rotate the rotating shaft, and the magnet and the posts are arranged at intervals along an extending direction of the rotating shaft; and
   wherein the magnet comprises a first magnet and a second magnet arranged at intervals along the axis of the rotating shaft, and the posts are located between the first magnet and the second magnet; the rotating magnetic field generated by the coil winding interacts with the first magnet and the second magnet respectively, to rotate the rotating shaft.

2. The blood pump according to claim 1, wherein each post comprises a rod portion, and a first head portion and a second head portion respectively disposed at both ends of the rod portion, the first magnet is arranged opposite to the first head portion, and the second magnet is arranged opposite to the second head portion.

3. The blood pump according to claim 1, wherein the rotor further comprises a flywheel arranged on the rotating shaft, and the magnet is fixed on the flywheel.

4. The blood pump according to claim 1, wherein an axial distance between the magnet and each post is ranged from 0.1 mm to 2 mm.

5. The blood pump according to claim 4, wherein the axial distance between the magnet and each post is ranged from 0.1 mm to 0.5 mm.

6. The blood pump according to claim 1, wherein the magnet further comprises a third magnet, and a fourth magnet, and the stator comprises a first stator and a second stator arranged along the axis of the rotating shaft, the first stator is located between the first magnet and the second magnet, and the second stator is located between the third magnet and the fourth magnet; and
   the coil winding of the first stator can generate a rotating magnetic field capable of interacting with the first magnet and the second magnet to rotate the rotating shaft; the coil winding of the second stator can generate a rotating magnetic field capable of interacting with the third magnet and the fourth magnet to rotate the rotating shaft.

7. The blood pump according to claim 6, wherein the rotor further comprises a first flywheel, a second flywheel and a third flywheel that are arranged on the rotating shaft at intervals along the axis of the rotating shaft, and the first magnet is assembled on the first flywheel, the second magnet and the third magnet are respectively assembled on the second flywheel, and the fourth magnet is assembled on the third flywheel.

8. The blood pump of claim 1, wherein the drive unit further comprises a distal bearing and a proximal bearing fixedly accommodated in the casing, the distal bearing and the proximal bearing are arranged along the axis of the rotating shaft, the distal bearing is closer to the impeller than the proximal bearing, and the rotating shaft passes through the distal bearing and is connected with the proximal bearing.

9. The blood pump according to claim 8, wherein the casing is respectively provided with a limiting groove configured for accommodating the distal bearing and a limiting groove configured for accommodating the proximal bearing.

10. The blood pump according to claim 1, wherein the drive unit further comprises a control member fixedly accommodated in the casing, the control member is electrically connected to the coil winding, and the casing is provided therein with a limiting groove configured for accommodating the control member.

11. The blood pump according to claim 1, wherein the casing comprises a first casing, a second casing and a third casing, and the third casing is sleeved outside the stator, the first casing and the second casing are respectively connected to two ends of the third casing, and the rotating shaft passes through the first casing and is connected to the impeller.

12. The blood pump according to claim 1, wherein the casing is provided with a positioning structure, and connection wires of the coil winding are fixed in the positioning structure.

13. A blood pump, comprising:
a cannula, provided with a blood flow inlet and a blood flow outlet;
an impeller, disposed in the cannula; and
a drive unit, capable of driving the impeller to rotate and comprising:
a casing, connected to the cannula;
a rotor, comprising a rotating shaft and a magnet, wherein the rotating shaft is partially accommodated in the casing, and partially extends to an outside of the casing and is connected with the impeller; the magnet is accommodated in the casing and arranged on the rotating shaft; and
a stator, comprising a plurality of posts arranged around an axis of the rotating shaft, and a coil winding around peripheries of the posts, wherein the coil winding capable of generating a rotating magnetic field that interacts with the magnet to rotate the rotating shaft, and the magnet and the posts are arranged at intervals along an extending direction of the rotating shaft; and
wherein the magnet comprises a first magnet and a second magnet arranged at intervals along an axis of the rotating shaft, and the stator comprises a first stator and a second stator arranged at intervals along the axis of the rotating shaft, the rotating magnetic field generated by the coil winding of the first stator capable of interacting with the first magnet to rotate the rotating shaft, the rotating magnetic field generated by the coil winding of the second stator capable of interacting with the second magnet to rotate the rotating shaft.

14. The blood pump according to claim 13, wherein the rotor further comprises a flywheel arranged on the rotating shaft, the flywheel is located between the first stator and the second stator, and the first magnet and the second magnet are respectively fixed on the flywheel.

15. The blood pump according to claim 13, wherein the first stator and the second stator respectively comprise a back plate, and the back plate of the first stator is connected to an end of each post of the first stator, the other end of each post of the first stator extends toward a direction close to the first magnet, and the back plate of the second stator is connected to an end of each post of the second stator, and the other end of each post of the second stator extends toward a direction close to the second magnet.

16. The blood pump according to claim 13, wherein two first magnets are provided, and the two ends of each post of the first stator respectively extend toward a direction close to the two first magnets; the second stator further comprises a back plate connected to one end of each post of the second stator, and the other end of each post of the second stator extends toward a direction close to the second magnet.

17. A blood pump, comprising:
a cannula, provided with a blood flow inlet and a blood flow outlet;
an impeller, disposed in the cannula; and
a drive unit, capable of driving the impeller to rotate and comprising:
a casing, connected to the cannula;
a rotor, comprising a rotating shaft and a magnet, wherein the rotating shaft is partially accommodated in the casing, and partially extends to an outside of the casing and is connected with the impeller; the magnet is accommodated in the casing and arranged on the rotating shaft; and
a stator, comprising a plurality of posts arranged around an axis of the rotating shaft, and a coil winding around peripheries of the posts, wherein the coil winding capable of generating a rotating magnetic field that interacts with the magnet to rotate the rotating shaft, and the magnet and the posts are arranged at intervals along an extending direction of the rotating shaft; and
wherein each post comprises a rod portion and a head portion fixed at an end of the rod portion, the head portion is arranged opposite to the magnet; the stator further comprises a back plate connected with an end of the rod portion away from the head portion.

* * * * *